United States Patent [19]

Schwarze et al.

[11] Patent Number: 4,905,672
[45] Date of Patent: Mar. 6, 1990

[54] THROMBOSES FORMATION BY MEANS OF SHOCK WAVES

[75] Inventors: Werner Schwarze, Stockach; Walter Brendel, Planegg, both of Fed. Rep. of Germany

[73] Assignee: Dornier Medizintechnik GmbH, Fed. Rep. of Germany

[21] Appl. No.: 243,106

[22] Filed: Sep. 2, 1988

Related U.S. Application Data

[63] Continuation of Ser. No. 941,169, Dec. 12, 1986, abandoned.

[30] Foreign Application Priority Data

Dec. 14, 1985 [DE] Fed. Rep. of Germany ....... 3544344

[51] Int. Cl.⁴ ............................................. A61B 17/12
[52] U.S. Cl. ................................................. 128/24 A
[58] Field of Search ..................... 128/24 A, 328, 804; 604/22

[56] References Cited

U.S. PATENT DOCUMENTS

| 3,352,303 | 11/1967 | Delaney | 128/24 A |
| 3,735,755 | 5/1973 | Eggleton et al. | 128/24 A |
| 4,530,358 | 7/1985 | Forssmann et al. | 128/328 |

FOREIGN PATENT DOCUMENTS

| 3240691 | 4/1984 | Fed. Rep. of Germany | 128/328 |
| 3241026 | 5/1984 | Fed. Rep. of Germany | 128/328 |

*Primary Examiner*—Ruth S. Smith
*Attorney, Agent, or Firm*—Burns, Doane Swecker & Mathis

[57] ABSTRACT

A process and device for treating pathological neoformations. The process is carried out by thrombosis formation in blood vessels by means of shock waves. The method is particularly effective for treating the neoformations with minimal effect upon healthy tissue.

5 Claims, 2 Drawing Sheets

THROMBOSES FORMATION BY MEANS OF SHOCK WAVES

This application is a continuation of application Ser. No. 941,169, filed Dec. 12, 1986, now abandoned.

BACKGROUND OF THE INVENTION

The present invention generally relates to the treatment of pathological neoformations. More specifically, the present invention relates to a method and device for carrying out the method of thromboses formation by means of shock waves.

Processes are known which destroy kidney stones in living bodies by means of shock waves. Such processes are generally based on the physical principle that when shock waves act upon interfaces at which the acoustic impedance changes nonuniformly, they are reflected as pressure waves or tensile waves according to the acoustic characteristics of the interfaces. If the compressive or the tensile strength of the material is exceeded during this treatment, the material is mechanically destroyed. For disintegrating kidney stones, focusing methods have been used wherein as the shock waves are passed through the tissue, the stress on the tissue is maintained at low levels. Furthermore, by utilizing such focusing methods, high concentrations of energy in the area of the kidney stone are achieved.

It is also known that if instead of a kidney stone, there is healthy tissue in the focus of the shock wave, this tissue can be destroyed by the shock wave. It has been suggested that this effect be used for destroying benign tumors since with such tumors there is no danger of metastases occurring. In the case of malignant tumors, however, although the cancer cells can be destroyed by this method, a large portion of the surrounding healthy tissue must also be destroyed in order to avoid the formation of metastases. Furthermore, there is also the danger of cells which have been only partially destroyed metastasizing by starting to proliferate on the spot or by being transferred by the blood stream to other parts of the body.

SUMMARY AND OBJECTS OF THE INVENTION

In view of the foregoing limitations and shortcomings of the above described processes, as well as other disadvantages not specifically mentioned above, it should be apparent that there still exists a need in the art for a method which would prevent the growth and spread of pathological neoformations, i.e., tumors, within the body. It is therefore, a primary objective of this invention to fulfill that need by providing a process and device which is non-invasive, but which can effectively treat tumors within the body.

The present invention is a method for treating pathological neoformations. The treatment comprises establishing shock waves at energy levels below the level at which cells are destroyed, and subjecting blood vessels which supply blood to the pathological neoformations to the shock waves to cause thromboses formation in the blood vessels.

BRIEF DESCRIPTION OF THE DRAWINGS

The present invention is further explained by reference to the drawings in which;

FIG. 5 shows a device for thromboses formation by means of shock waves.

DETAILED DESCRIPTION OF THE PREFERRED EMBODIMENTS

Figure 1:
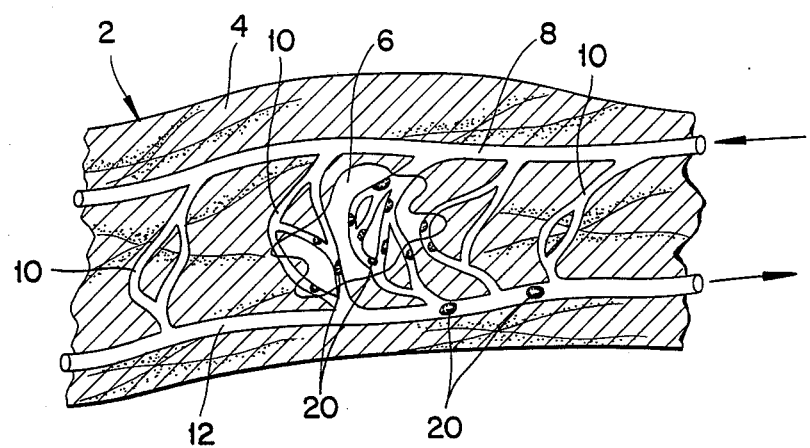
FIG. 1 shows a pathological neoformation with surrounding healthy tissue in a diagrammatic view.

The process of the present invention involves establishing shock waves of an energy level below that at which tissue cells are destroyed, to act upon the blood vessels which supply pathological neoformations with blood. As the result of this treatment, changes in the walls of the blood vessels result, which in turn, lead to thromboses formation in the blood vessels.

In contrast to the blood vessels which supply blood to tumor tissues, larger vessels and blood vessels of healthy tissues have thicker walls comprising both an endothelial layer and a basal membrane, and in the case of arterioles and larger venoles, a muscular layer. Consequently, blood vessels of this type are resistant to the changes experienced by the tumor blood vessels under the impact of shock waves of suitable therapeutical intensity.

The blood vessels of tumor tissues have primarily thin walls usually consisting only of an endothelial layer. Therefore, unlike blood vessels of healthy tissues, these vessels are particularly sensitive to changes caused by shock waves due to their special anatomy.

According to the present invention, the walls of the capillaries of a tumor are subjected to changes brought about by shock waves so that microthrombi are formed in these areas of the vessels. Therefore, the growth or metastases is minimized since the small blood vessels supplying the tumor with blood cannot function properly. Furthermore, cumulative formation of microthrombi will reinforce the above described effect and can also result in thromboses formation in the outgoing venoles.

It has been found that when other methods are combined with shock wave treatment, the above described effect is enhanced. For example, local hyperthermia of the pathological neoformation combined with shock wave treatment is particularly effective. Furthermore, administering medical preparations which aid in the coagulation of the blood during shock wave treatment has also been found to enhance the treatment. When combined with shock wave treatment, the injection of gases or particles will advantageously impede the flow of blood and cause multiple reflections of the shock waves in the target. Also, it has been found that when cytostatic substances are administered, they are taken up to a larger degree by the acoustically exposed cells due to the increased permeability of the membranes after the shock wave treatment, thereby reinforcing the effect of the cytostatic substances. Radiation treatment, such as X-ray treatment, also has been found to enhance the effects of shock wave treatment.

In accordance with the present invention, blood vessels which supply blood to pathological neoformations are subjected to shock waves. Preferably the shock waves are focused. However, in situations where the shock wave source or the neoformation is large, unfocused shock waves may be used.

In a particularly preferred embodiment of the present invention, the blood vessels of the pathological neoformation are acted upon by shock waves from different directions, e.g., at different angles. This "crossfireacoustic exposure" treatment has been found to be particularly effective in minimizing damage to healthy tissue.

In another preferred embodiment of the present invention, the process involves a continuous change in the direction of shock wave exposure. During this "oscillating acoustic exposure" treatment, the energy dose is kept constant.

In practicing the present invention, an exposure scheme is established for performing the shock wave treatment. Such a scheme is set up to calculate the pressure distribution in a particular space. From the knowledge about the distribution of pressure in the case of an individual shock, $i:=(1,\ldots,N)$, a cumulative distribution of pressure with N shocks can be calculated. This cumulative pressure distribution, called the "dose", can be described in a first approximation as follows:

$$\text{dose} = \sum_{i=1}^{N} p_i(X,Y,Z),$$

where N represents the number of shocks applied, and $p_i(X,Y,Z)$ represents the pressure at the point $(X,Y,Z)$ with the i-th shock.

In a diagrammatic view, FIG. 1 shows a section of tissue 2 consisting of healthy tissue 4 and a pathological neoformation (tumor) 6. The tumor is supplied with blood by the arteriole 8 which branches out into capillaries 10 in the area of the tumor. The blood flows back via venoles 12.

Figure 3:
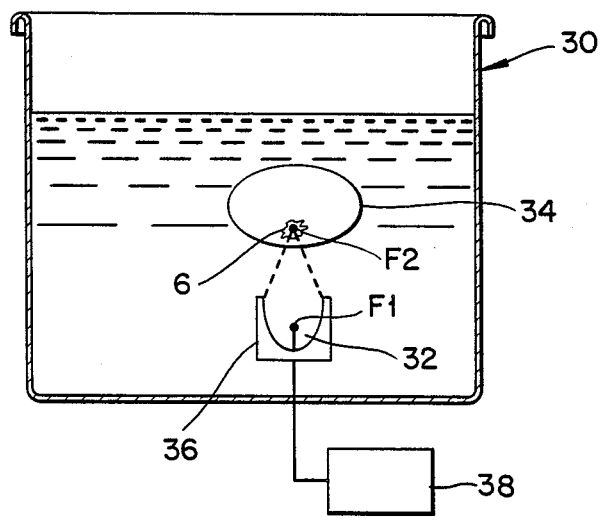
FIGS. 2-4 show the progressive change in the endothelial wall of the capillary during shock wave treatment.
Figure 2:
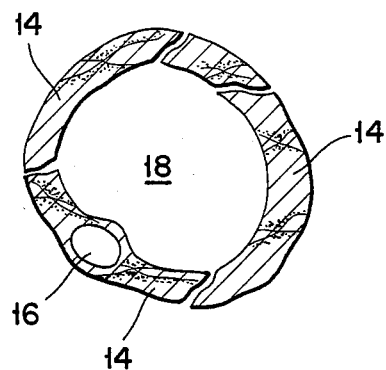
Figure 3:
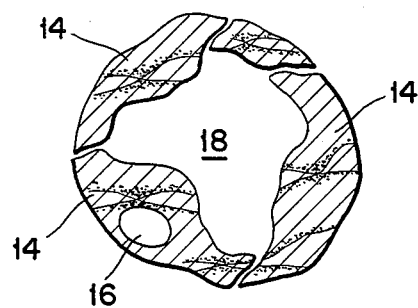
Figure 4:
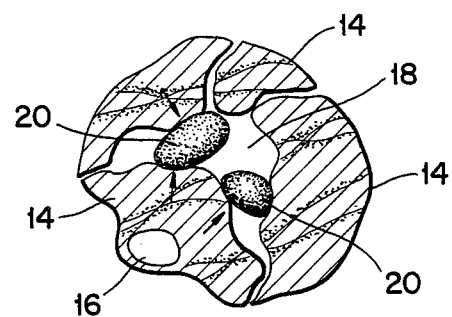

The blood vessels 10 running through the tumor 6 have thinner walls than healthy capillaries and consist only of an endothelial layer. The diameter of such capillaries as represented in FIG. 2 is about 8 microns. The capillary, which includes flat endothelial cells 14 with a nucleus 16, linked together in a stave-type manner, is subjected to a focused shock wave. As shown in FIG. 3, during this step the endothelial cells first swell and the cross-sectional area 18 for blood flow is reduced. If the capillary is serially acted upon by shock waves at a higher energy level, the endothelial layer forming the wall of the capillary is eventually irreversibly changed as shown in FIG. 4. The capillary can no longer function properly, as erythrocytes penetrate into the tissue and the supply of blood to the tumor 6 is reduced or stopped altogether. As a result, at these points the blood supply to the tumor is partially or entirely blocked so that the tumor receives at most an insufficient supply of blood and its growth is minimized or stopped altogether.

Black dots 20 in FIG. 1 illustrate the occurrence of thromboses formation resulting from shock wave treatment. At these points the blood supply to the tumor is either partially or entirely blocked. As a result, the tumor receives an insufficient supply of blood, and its growth is checked.

FIG. 5 schematically shows a device for carrying out the method of the present invention. Within a water-filled tub 30 is a shock wave source 32 and a patient 34. The shock wave source is preferably located in the focus F1 of an ellipsoid of revolution 36. Shock waves emanating from the shock wave source are concentrated in the focus F2 where the tissue to be treated is located. Shock wave source 32 is driven by power supply 38.

The pressure in the focus is typically between about 1,000 and 2,000 bar. Spark discharge, lasers, electromechanical sources or piezo electric generators can be employed to produce shock waves. Also, instead of an ellipsoid, spherical segments or optical lenses can be used for focusing.

For the purpose of oscillating acoustic exposure, the ellipsoid 36, together with the shock wave source 32, can move around F2 in an oscillating manner. Alternatively, the patient's body 34 can perform oscillating movements around F2 while the ellipsoid is stationary.

Although only preferred embodiments of the invention are specifically illustrated and described above, it will be appreciated that many modifications and variations of the present invention are possible in light of the above teachings, and are within the purview of the appended claims without departing from the spirit and intended scope of the invention.

What is claimed is:

1. A method for treating a pathological neoformation in a living organism comprising (i) establishing shock waves at pressure levels below the level at which cells are destroyed but at a level sufficient to cause thrombosis formation, and (ii) subjecting blood vessels which supply blood to the pathological neoformation to the shock waves to cause thrombosis formation in the blood vessels thereby reducing blood flow to the pathological neoformation.

2. The method according to claim 1 wherein the shock waves are focused.

3. The method according to claim 1 wherein the blood vessels are subjected to shock waves from at least two different directions.

4. The method according to claim 1 wherein the blood vessels are continuously subjected to shock waves of a constant energy level in which the direction from which the shock waves are directed at the blood vessels changes continuously.

5. The method according to claim 1 further comprising at least one additional treatment, wherein the additional treatment is (iii) subjecting the pathological neoformation to hyperthermia, (iv) administering a blood coagulating preparation, (v) administering a cytostatic substance, (vi) treating with X-rays, (vii) injecting a means for impeding blood flow, or (viii) injecting a means for causing multiple reflections of the shock waves.

* * * * *